US00PP29119P3

(12) United States Plant Patent
Randag

(10) Patent No.: US PP29,119 P3
(45) Date of Patent: Mar. 13, 2018

(54) VARIETY OF CALLA LILY PLANT NAMED 'FURSA'

(50) Latin Name: *Zantedeschia sprengeri*
Varietal Denomination: Fursa

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 18 days.

(21) Appl. No.: 14/998,459

(22) Filed: Jan. 6, 2016

(65) Prior Publication Data

US 2016/0212921 P1 Jul. 21, 2016

Related U.S. Application Data

(60) Provisional application No. 62/125,226, filed on Jan. 15, 2015.

(51) Int. Cl.
*A01H 5/02* (2006.01)

(52) U.S. Cl.
USPC ..... Plt./490

(58) Field of Classification Search
USPC ..... Plt./490
CPC ..... A01H 5/0272
See application file for complete search history.

(56) References Cited

PUBLICATIONS http://www.sierteeltnet.nl/bloemen-planten/nieuws/funakoshi-en-fursa-officieel-gedoopt/; Apr. 7, 2013; 5 pages.*

* cited by examiner

*Primary Examiner* — Kent L Bell
(74) *Attorney, Agent, or Firm* — The Webb Law Firm

(57) ABSTRACT

'Fursa' is a new variety of calla lily plant having inflorescences with a yellow-colored spathe and throat spot that produces 4-20 inflorescences per tuber. The height of the top of an inflorescence above the soil can reach up to 50 cm, and the leaves are dark green with transparent maculations present and have a leathery texture.

4 Drawing Sheets

Botanical classification: *Zantedeschia sprengeri*.
Varietal denomination: 'FURSA'.

CROSS REFERENCE TO RELATED APPLICATION

This application claims the benefit of U.S. Provisional Patent Application Ser. No. 62/125,226, having a filing date of Jan. 15, 2015, and entitled "Varieties of Calla Lily Plants", the entire disclosure of which is incorporated herein by reference.

BACKGROUND OF THE NEW PLANT

The present invention comprises a new and distinct cultivar of calla lily, botanically known as *Zantedeschia sprengeri* and hereinafter referred to by the cultivar name 'Fursa'.

'Fursa' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as 'Summer Sun' (female parent, unpatented) with a *Zantedeschia sprengeri* selection referred to as Z041922 (male parent, unpatented). 'Fursa' was selected in 2009 by the inventor in 't Zand, The Netherlands as one flowering plant within the progeny of the stated cross.

The first act of asexual reproduction of 'Fursa' by tissue culture was performed by the inventor in September of 2009 in 't Zand; The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Fursa' which, in combination, distinguish this calla lily as a new and distinct cultivar:

1. Large, yellow-colored spathe;
2. Large, dark purple throat spot located at the inner bottom surface of the spathe; and
3. High inflorescence production.

Further, when compared to calla lily plant named 'Yellow Jacket BLZ' (U.S. Plant Pat. No. 20,217), 'Yellow Jacket BLZ' has an upper surface spathe color of Yellow Group RHS 7A and a lower surface spathe color of Yellow Group RHS 7B, whereas 'Fursa' has an upper and lower surface spathe color that varies between Yellow-Orange Group RHS 14A and 14B, with variations of Yellow-Green Group RHS 144A and 144B present at the outer tip and base.

Table 1 provides similarities and differences of 'Fursa' to its parents, *Zantedeschia sprengeri* selections 'Summer Sun' and Z041922.

TABLE 1

| 'Fursa' | Similarities | Differences |
|---|---|---|
| 'Summer Sun' | White spots on leaves<br>Plant height | Spathe color<br>Number of inflorescences<br>Spathe shape |
| Z041922 | Leaf shape<br>Number of inflorescences<br>Spathe shape | Spathe size<br>Spathe color |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
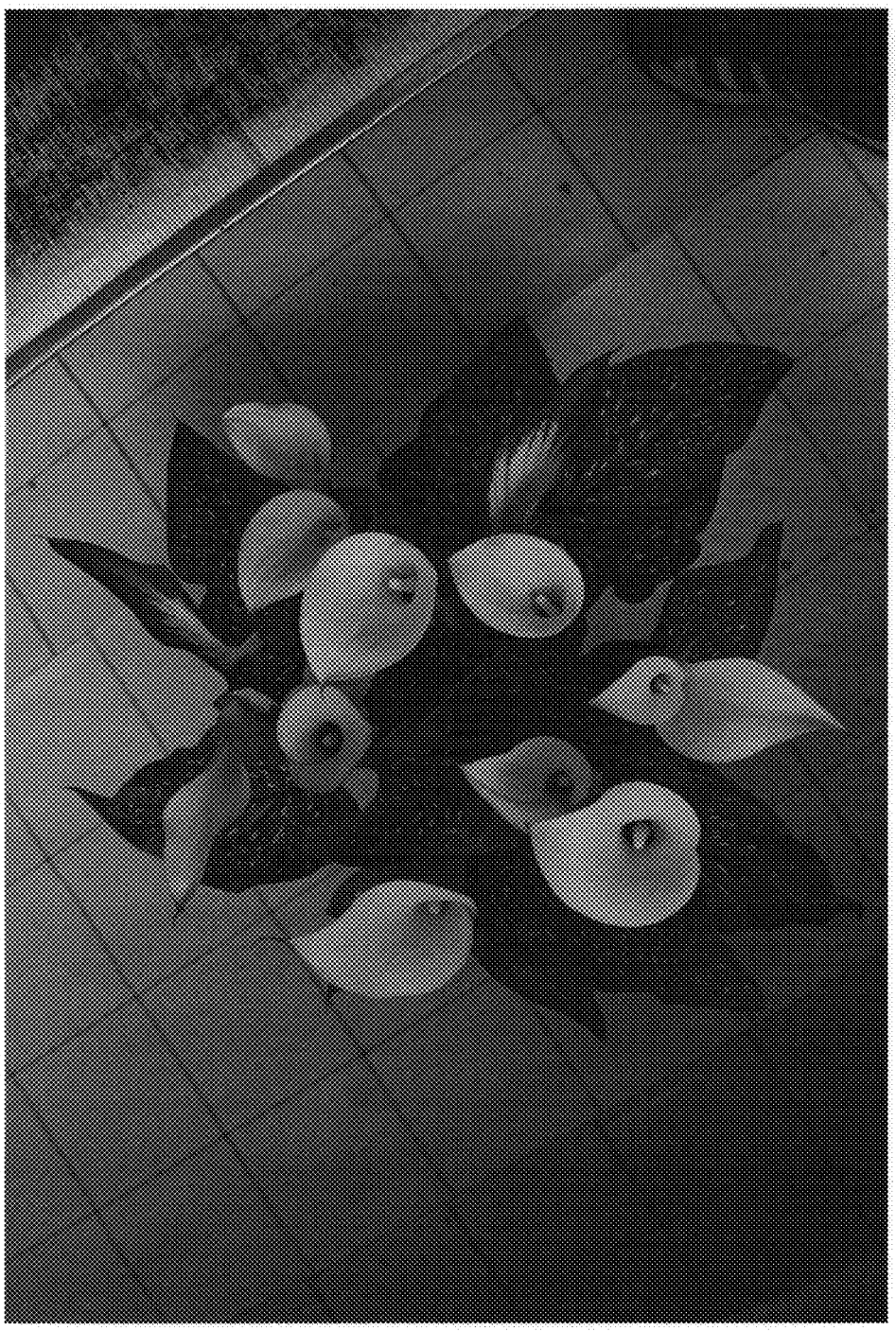
FIG. 1 is a photograph of a plant of the new variety.
Figure 2:
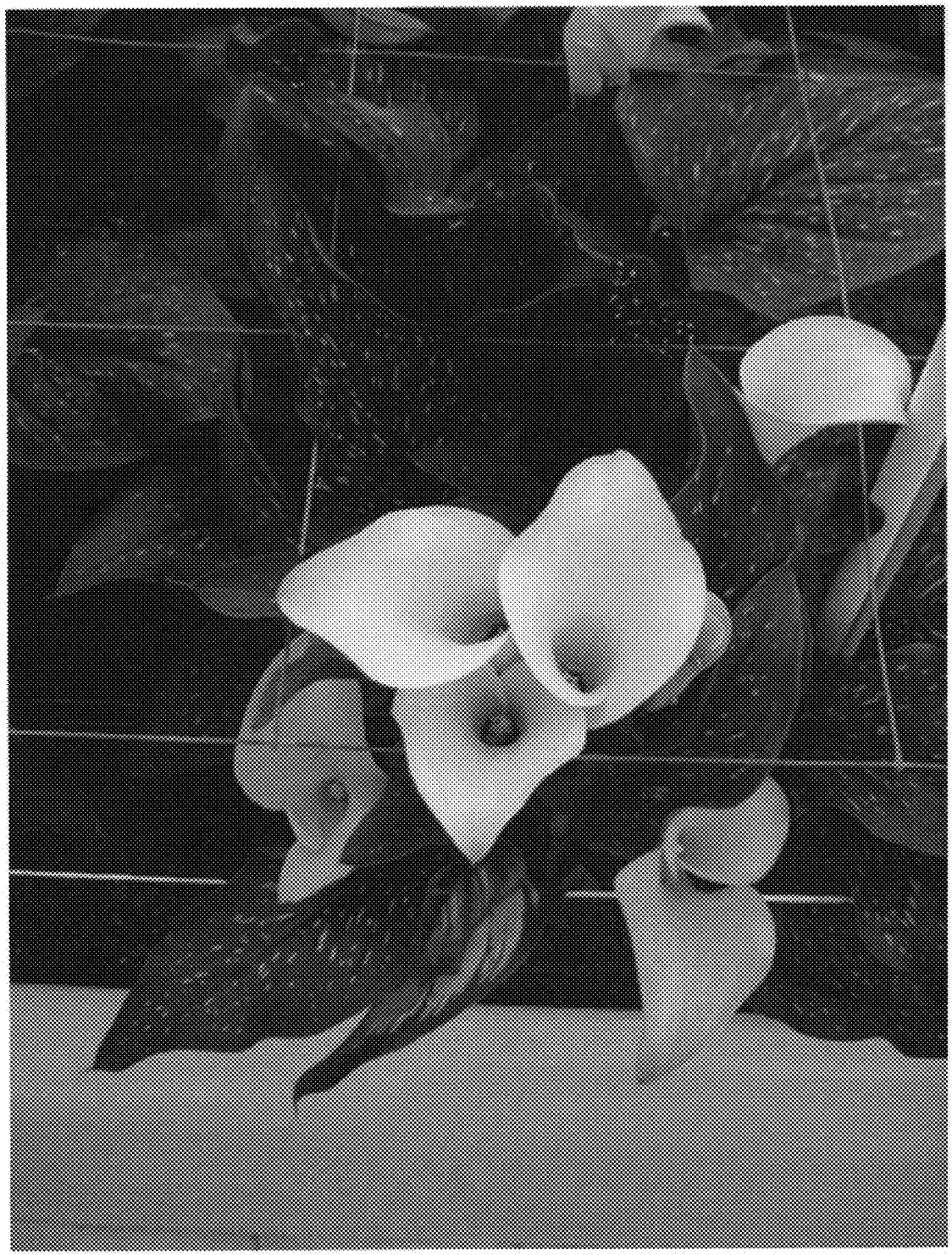
FIG. 2 is a photograph of a plant of the new variety.
Figure 3:
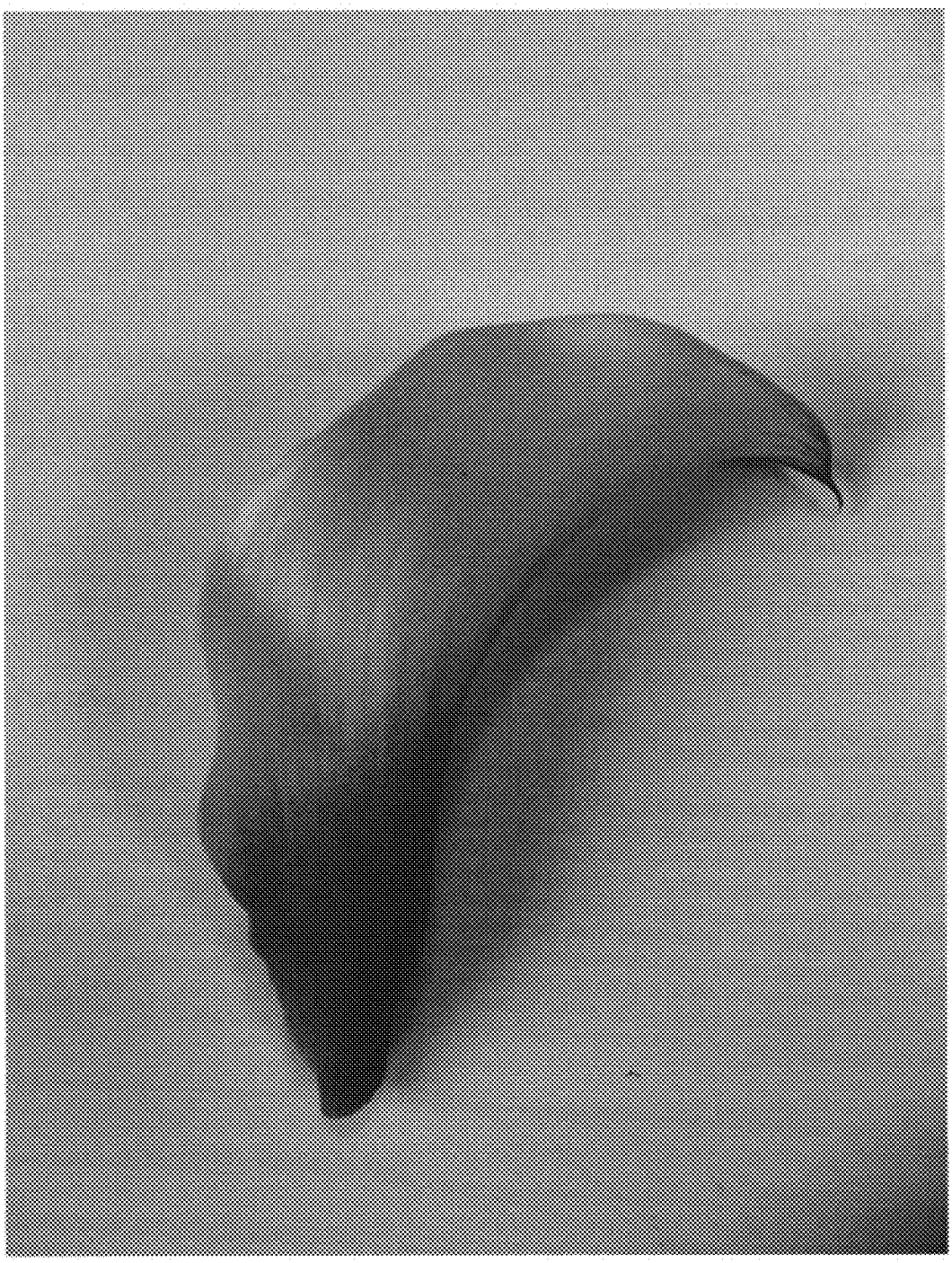
FIG. 3 is a photograph of a side view of the outer surface of a spathe of the new variety.
Figure 4:
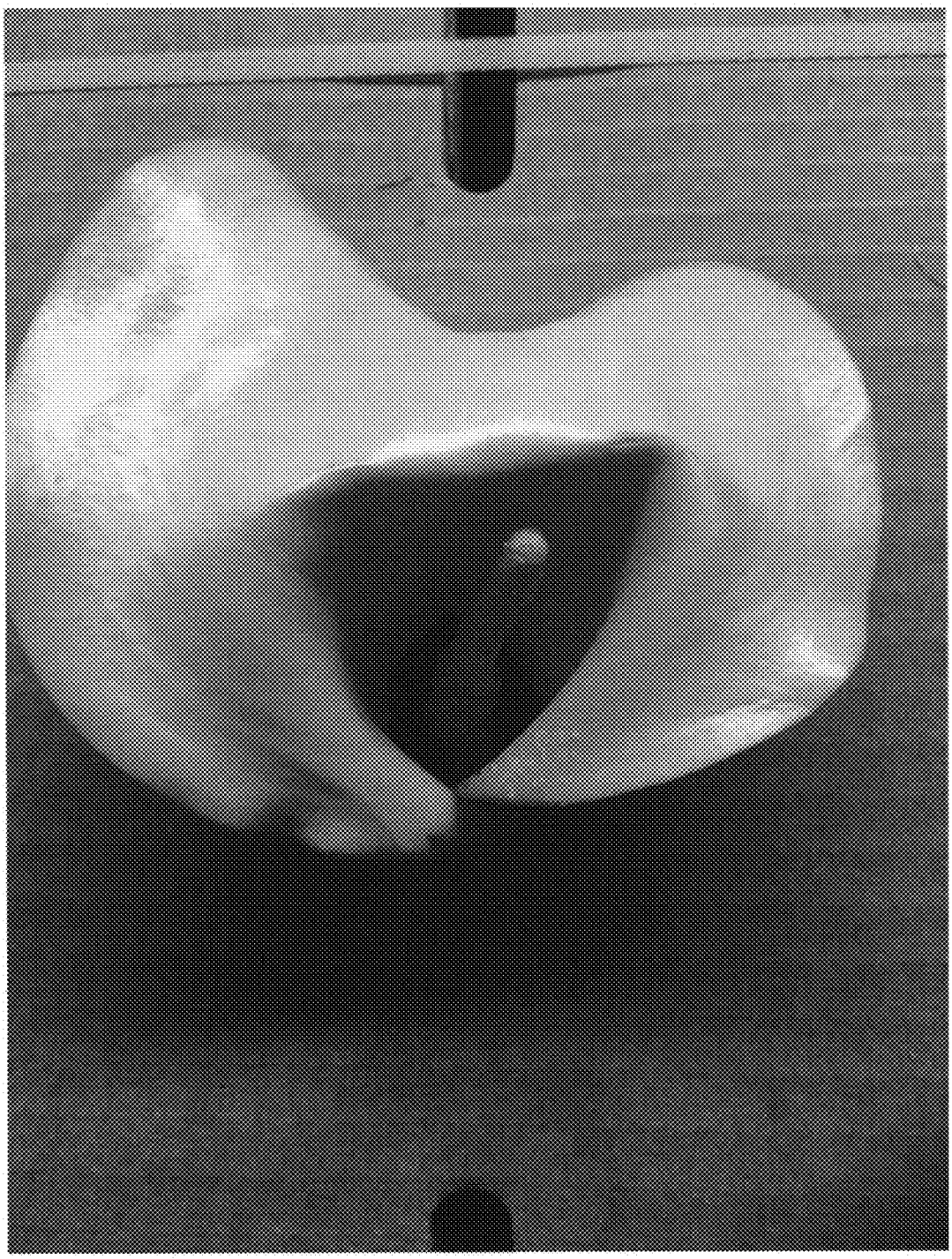
FIG. 4 is a photograph of a top view of a spathe of the new variety.

Size:

*Height of the leaf canopy above the soil.*—10-35 cm.

*Height of top of inflorescence above the soil.*—15-50 cm.

*Diameter.*—15-50 cm.

Form: Erect.

Number of inflorescences per tuber:

*Size* 14-16 *cm in diameter.*—4-8 inflorescences.

*Size* 16-18 *cm in diameter.*—8-13 inflorescences.

*Size* 18-20 *cm in diameter.*—8-20 inflorescences.

Branches:

*Character.*—Many; like the variety 'Odessa' (U.S. Plant Pat. No. 18,833).

*Color.*—Between Green Group RHS 137A and Greyed-Purple Group RHS N186A.

Leaves:

*Size.*—Width: 4-15 cm. Length: 10-20 cm.

*Number per plant.*—20-40.

*Shape.*—Lanceolate.

*Color.*—Upper surface: Green Group RHS 137A to 137B with streaks of Yellow-Orange Group RHS 14A to 14B, and having transparent maculations between White Group RHS 155A and N155A. Lower surface: Green Group RHS 137A to 137B with streaks of Yellow-Orange Group RHS 14A to 14B, and having transparent maculations between White Group RHS 155A and N155A.

*Apex.*—Apiculate.

*Base.*—Truncate.

*Margin.*—Undulate; having a color of Green Group RHS 137A to 137B.

*Veins.*—Configuration: Pinnate. Color: Upper Surface: Green Group RHS 137A to 137B. Lower Surface: Yellow-Green Group RHS 146B to 147B.

*Surface quality.*—Leathery.

*Petiole.*—Length: 10-25 cm. Diameter: 6 mm. Color: The base is White Group RHS 155A, and the upper part is Green Group RHS 137A to 137B.

Roots:

*Color.*—White.

*Branching.*—Similar to other *Zantedeschia* varieties.

The Inflorescence and Seeds

Spathe:

*Size.*—Length (measured from opening to tip): 4-8 cm. Width: 4-7 cm. Height: 4-10 cm.

*Color.*—Upper surface: Varies between Yellow-Orange Group RHS 14A and 14B, with variations of Yellow-Green Group RHS 144A and 144B at the outer tip surface. Lower surface: Varies between Yellow-Orange Group RHS 14A and 14B, with variations of Yellow-Green Group RHS 144A and 144B at the outer base surface, and having a throat spot that varies between Purple Group RHS N77A and 79A at the inner bottom spathe surface.

*Vein color.*—Between Yellow-Orange Group RHS 14A and 14B.

*Shape.*—Cupped.

*Apex.*—Rounded.

*Margin.*—Entire.

Spadix:

*Size.*—Length: 24-45 mm. Diameter: 3-10 mm.

*Color.*—Between Yellow-Orange Group RHS 17A and 17B.

*Position relative to spathe.*—Upright.

Peduncle:

*Size.*—Length: 10-37 cm. Diameter: 3-13 mm.

*Color.*—The upper part is between Yellow-Green Group RHS 144A and 144B, and the lower part is Green-White Group RHS 157C.

Reproductive organs:

*Location of female organs.*—Basal position of the spadix.

*Location of male organs.*—Upper position of the spadix.

*Perianth.*—Conspicuous.

*Stamens.*—Presence: Not visible before pollen release. Number: More than 20. Pollen amount: Similar to 'Picasso' (U.S. Plant Pat. No 15,282). Color: Between White Group RHS 155A and 155B.

*Anther.*—Shape: Round. Length: Less than 1 mm. Color: Between Yellow-Orange Group RHS 17A and 17B.

*Filament.*—Length: Less than 1 mm. Color: Between White Group RHS 155A and 155B.

*Pistils.*—Number: 15 to 30. Length beyond perianth: About 1 mm.

*Stigma.*—Shape: Round. Size: Less than 1 mm.

*Style.*—Length: Less than 1 mm. Color: Between Yellow-Orange Group RHS 16A and 16B.

*Ovaries.*—Texture: Smooth. Length: Between 1 to 10 mm. Width: Between 1 to 10 mm. Color: Top color is between Green Group RHS 143C and 143D, bottom color is from White Group RHS 155B to Green-White Group RHS 157C.

Seeds:

*Length.*—4-7 mm.

*Width.*—3-6 mm.

*Color.*—Between Yellow-Green Group RHS 150A and 151A.

*Amount.*—Between 1-60.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July.

Lastingness: About two weeks on the plant.

Fragrance: None.

I claim:

1. A new and distinct variety of calla lily plant named 'Fursa' as herein described and illustrated.

* * * * *